(12) United States Patent
Meyer et al.

(10) Patent No.: US 8,597,614 B2
(45) Date of Patent: Dec. 3, 2013

(54) DIAGNOSIS AND TREATMENT OF MOOD DISORDERS

(75) Inventors: Jeffrey Hugh Meyer, Toronto (CA); Nathalie Ginovart, Annemasse (FR)

(73) Assignee: Centre for Addiction and Mental Health, Toronto (CA)

( * ) Notice: Subject to any disclaimer, the term of this patent is extended or adjusted under 35 U.S.C. 154(b) by 1023 days.

(21) Appl. No.: 11/997,406

(22) PCT Filed: Aug. 2, 2006

(86) PCT No.: PCT/CA2006/001277
§ 371 (c)(1),
(2), (4) Date: Jun. 12, 2008

(87) PCT Pub. No.: WO2007/014467
PCT Pub. Date: Feb. 8, 2007

(65) Prior Publication Data
US 2008/0274051 A1    Nov. 6, 2008

Related U.S. Application Data

(60) Provisional application No. 60/704,872, filed on Aug. 3, 2005.

(51) Int. Cl.
*A61K 51/00* (2006.01)
*A61M 36/14* (2006.01)

(52) U.S. Cl.
USPC .......................... 424/1.11; 424/1.69

(58) Field of Classification Search
None
See application file for complete search history.

(56) References Cited

PUBLICATIONS

Bergstrom et al. Eur. J. Clin Phamacol. (1997) 52: 121-128.*
Logan et al. J. Cereb. Blood Flow Metab. (1990) 10: 740-747.*
Fowler et al. Science (1987) 235: 481-485.*
Fowler et al. Naunyn-Schmiedberg's Arch. Pharmacol. (1980) 311: 263-272.*
Bergstrom et al. (1997) "11C-harmine as tracer for monoamine oxidase A (MAO-A): in vitro and in vivo studies" Nuc. Med. Biol. 24(4):287-293 (Abstract).
Bergstrom et al. (1997) "MAO-A inhibition in brain after dosing with esuprone, moclobemide and placebo in healthy volunteers: in vivo studies with positron emission tomography" Eur. J. Clin. Pharmacol. 52(2):121-128 (Abstract).
Reveley et al. (1981) "Increased platelet monoamine oxidase activity in affective disorders" Psychopharmacology 73:257-260.
Sandler et al. (1981) "Human platelet monoamine oxidase activity in health and disease: a review" J. Clin. Pathol. 34:292-302.
Schneider et al. (1986) "Platelet monoamine oxidase activity in elderly depressed outpatients" Biol. Psychiatry 21:1360-1364.
Trivedi et al. (1988) "Platelet monoamine oxidase in unipolar & bipolar depression" Indian J. Med. Res. 88:165-168.

White et al. (1981) "Elevated platelet monoamine oxidase activity in patients with nonendogenous depression" Am. J. Psychiatry 137(10):1258-1259.
International Search Report of PCT/CA2006/001277 mailed Nov. 28, 2006.
Written Opinion of PCT/CA2006/001277 mailed Nov. 28, 2006.
Meyer, et al., (2004) "Brain Serotonin Transporter Binding Potential Measured With Carbon 11-Labeled DASB Positron Emission Tomography", Arch Gen Psychiatry, 61:1271-1279.
Fowler, et al., (1987) "Mapping human brain monoamine oxidase A and B with carbon eleven-labeled suicide inactivators and PET", Science, 235: 481-485.
Fowler, et al., (1980) "Titration of Human Brain Monoamine Oxidase -A and -B by Clorgyline and L-Deprenil", Naunyn-Schmiedeberg's Arch. Pharmacol., 311: 263-272.
Logan, et al., (1990) "Graphical Analysis of Reversible Radioligand Binding from Time-Activity Measurements Applied to [N-11 C-methyl]-(–)-Cocaine PET Studies in Human Subjects", Journal of Cerebral Blood Flow and Metabolism, vol. 10 No. 5: 740-747.
Bergstrom, et al., (1997) "MAO-A inhibition in brain after dosing with esuprone, moclobemide and placebo in healthy volunteers: in vivo studies with positron emission tomography", Eur J Clin Pharmacol, 52: 121-128.
Galva, et al., (1995) "Effect of aging on lazabemide binding, monoamine oxidase activity and monoamine metabolites in human frontal cortex", J Neural Transm, 101: 83-94.
Meyer, et al., (2006) "Elevated Putamen D2 Receptor Binding Potential in Major Depression With Motor Retardation: An [11C] Raclopride Positron Emission Tomography Study", Am J Psychiatry, vol. 163(9): 1594-1602.
Meyer, et al., (2001) "Lower dopamine transporter binding potential in striatum during depression", NeuroReport, 12(18): 4121-4125.
Ranga, et al., (2002) "Biological Risk Factors in Late Life Depression", Society of Biological Psychiatry, 52: 185-192.
Fowler, et al., (1996) "Brain monoamine oxidase A inhibition in cigarette smokers", Proc. Natl. Acad. Sci. USA, 93:14065-14069.
Grote, et al., (1974) "A Study of Selected Catecholamine Metabolizing Enzymes: A Comparison of Depressive Suicides and Alcoholic Suicides with Controls", Journal of Neurochemistry, 23: 791-802.
Gottfries, et al., (1975) "Lowered Monoamine Oxidase Activity in Brains From Alcoholic Suicides", Journal of Neurochemistry, 25: 667-673.
Mann, et al., (1984) "Postmortem monoamine oxidase enzyme kinetics in the frontal cortex of suicide victims and controls", Acta psychiatr. scand., 69: 135-139.
Sherif, et al., (1991) "Brain Gamma-aminobutyrate Transaminase and Monoamine Oxidase Activities in Suicide Victims", Eur Arch Psychiatry Clin Neurosci, 241: 139-144.
Ordway, et al (1999) "Quantitative distribution of monoamine oxidase A in brainstem monoamine nuclei is normal in major depression", Brain Research, 847: 71-79.

(Continued)

*Primary Examiner* — Michael G Hartley
*Assistant Examiner* — Sean R Donohue
(74) *Attorney, Agent, or Firm* — Suzannah K. Sundby, Esq.; Smith, Gambrell & Russell, LLP

(57) ABSTRACT

The present invention relates to the diagnosis, treatment and monitoring of mood disorders. For example, a diagnosis may be performed by determining whether a monoamine oxidase in a vertebrate is elevated compared to a healthy control subject. Methods of monitoring treatments and methods for identifying treatments for mood disorders are also provided.

14 Claims, 3 Drawing Sheets

(56) References Cited

PUBLICATIONS

Kinemuchi, et al., (1984), "Substrate Specificities of the Two Forms of Monoamine Oxidase", Monoamine Oxidase and Disease, 53-62.

Saura, et al., (1996) "Molecular Neuroanatomy of Human Monoamine Oxidases A and B Revealed by Quantitative Enzyme Radioautography and in Situ Hybridization Histochemistry", Neuroscience, vol. 70(3): 755-774.

Fowler, et al., (1979) "Substrate-Selective Interaction Between Monoamine Oxidase and Oxygen", Monoamine Oxidase: Structure, Function, and Altered Functions, 145-151.

Konradi, et al., (1988) "Topographic Immunocytochemical Mapping of Monoamine Oxidase-A, Monoamine Oxidase-B and Tyrosine Hydroxylase in Human Post Mortem Brain Stem", Neuroscience, vol. 26(3): 791-802.

Finberg, et al., (1994) "Modification of cerebral cortical noradrenaline release by chronic inhibition of MAO-A", J Neural Transm, 41: 123-125.

Adell, et al., (1996) "Action of Harman (1-methyl-B-carboline) on the Brain: Body Temperature and in Vivo Efflux of 5-HT from Hippocampus of the Rat", Neuropharmacology, vol. 35(8): 1101-1107.

Celada, et al., (1993) "Monoamine oxidase inhibitors increase preferentially extracellular 5-hydroxytryptamine in the midbrain raphe nuclei. A brain microdialysis study in the awake rat", Naunyn-Schmiedeberg's Arch Pharmacol, 347: 583-590.

Haefely, et al., (1992) "Biochemistry and pharmacology of moclobemide, a prototype RIMA", Psychopharmacology, 106: S6-S14.

Evrard, et al., (2002) "Altered regulation of the 5-HT system in the brain of MAO-A knock-out mice", European Journal of Neuroscience, 15: 841-851.

Konradi, et al., (1989) "Demonstration of Monoamine Oxidase-A and -B in the Human Brainstem by a Histochemical Technique", Neuroscience, vol. 33(2): 383-400.

Cases, et al., (1995) "Aggressive Behavior and Altered Amounts of Brain Serotonin and Norepinephrine in Mice Lacking MAOA", Science, 268: 1763-1766.

Finberg, et al., (1994) "Modification of cerebral cortical noradrenaline release by chronic inhibition of MAO-A", J Neural Trans, 41: 123-125.

Finberg, et al., (1993) "Chronic inhibition of monoamine oxidase type A increases noradrenaline in rat frontal cortex", Naunyn-Schmiedeberg's Arch Pharacol, 347: 500-505.

Hranilovic, et al., (1996) "Identification of serotonin transporter mRNA in rat platelets", J Neural Transm, 103: 957-965.

Adachi, et al., (2001) "Oxygen inhalation enhances striatal dopamine metabolism and monoamineoxidase enzyme inhibition prevents it: a microdialysis study", European Journal of Pharmacology, 422: 61-68.

Wayment, et al., (2001) "Characterization of Extracellular Dopamine Clearance in the Medial Prefrontal Cortex: Role of Monoamine Uptake and Monoamine Oxidase Inhibition", The Journal of Neuroscience, 21: 35-44.

Moll, et al., (1990) "Immunofluorescence cytochemistry on thin frozen sections of human substantia nigra for staining of monoamine oxidase A and monoamine oxidase B: a pilot study", J Neural Transm, 32: 67-77.

Hochstrasser, et al., (2001) "Prophylactic effect of citalopram in unipolar, recurrent depression", British Journal of Psychiatry, 178: 304-310.

Bergstrom, et al., (1997) "Synthesis of Some 11C-Labelled MAO-A Inhibitors and Their in Vivo Uptake Kinetics in Rhesus Monkey Brain", Nuclear Medicine & Biology, 24: 381-388.

Ginovart, et al., (2006) "Positron emission tomography quantification of [11C]-harmine binding to monoamine oxidase-A in the human brain", Journal of Cerebral Blood Flow & Metabolism, 26: 330-344.

Bergstrom, et al., (1997) "11C-Harmine as a Tracer for Monoamine Oxidase A (MAO-A): in Vitro and in Vivo Studies", Nuclear Medicine & Biology, 24: 287-293.

Bottlaender, et al., (2003) "Mapping the Cerebral Monoamine Oxidase Type A: Positron Emission Tomography Characterization of the Reversible Selective Inhibitor [11C]Befloxatone", The Journal of Pharmacology and Experimental Therapeutics, vol. 305(2): 467-473.

Erlandsson, et al., (2005) "Measuring SSRI occupancy of SERT using the novel tracer [123I]ADAM: a SPECT validation study", European Journal of Nuclear Medicine and Molecular Imaging, vol. 32(11): 1329-1336.

Prunier, et al., (2003) "Quantification of Dopamine Transporter by 123I-PE2I SPECT and the Noninvasive Logan Graphical Method in Parkinson's Disease", J Nucl Med, 44: 663-670.

Wilson, et al., (2003) "Determination of the Arterial Input Function of the MAO-A Inhibitor [11C]-Harmine in Human Subjects", J. Label Compd. Radiopharm, 46:S367, Abstract provided.

Bolo, et al., (2000) "Brain Pharmacokinetics and Tissue Distribution in Vivo of Fluvoxamine and Fluoxetine by Flourine Magnetic Resonance Spectroscopy", Neuropsychopharmacology, vol. 23(4): 428-438.

Henry, et al., (2000) "Brain Kinetics of Paroxetine and Fluoxetine on the Third Day of Placebo Substitution: A Flourine MRS Study", Am J Psychiatry, vol. 157(9): 1506-1508.

Iga, et al., (2005) "Serotonin transporter mRNA expression in peripheral leukocytes of patients with major depression before and after treatment with paroxetine", Neuroscience Letters, 389: 12-16.

Malison, et al., (1998) "Reduced Brain Serotonin Transporter Availability in Major Depression as Measured by [123I]-2B-carbomethoxy-3B-(4-iodophenyl) tropane and Single Photon Emission Computed Tomography", Society of Biological Psychiatry, 44: 1090-1098.

Blais, et al., (1997) "A Psychometric Evaluation of the DSM-IV Personality Disorder Criteria", Journal of Personality Disorders, vol. 11(2): 168-176.

* cited by examiner

Fig. 1. Comparison of MAO-A DVs between depressed and healthy subjects. On average MAO-A DVs was elevated by 34 percent, or two standard deviations, in depressed individuals. Differences between groups were highly significant in each region: * $p=0.001$,  $p<0.0001$, * $p<0.00001$.

DIAGNOSIS AND TREATMENT OF MOOD DISORDERS

This application is a 371 national phase entry of PCT/CA2006/001277, filed 2 Aug. 2006, which claims the benefit of U.S. Patent Application No. 60/704,872, filed 3 Aug. 2005.

FIELD OF INVENTION

The present invention relates to the diagnosis and treatment of mood disorders.

BACKGROUND OF THE INVENTION

In major depressive disorder, there is substantial evidence that monoamines are low. Monoamines are chemicals and include, but are not limited to, the chemicals serotonin, norepinephrine and dopamine.

In major depressive episodes of major depressive disorders (MDE), there is a substantial accumulation of evidence that serotonin lowering processes exist. 5-HT stores may be low during MDE because 5-HT metabolite 5-hydroxyindoleacetic acid concentrations are often low in cerebrospinal fluid during MDE. It is thought that 5-HT release after d-fenfluramine administration is reduced during MDE because the prolactin release after d- and (d,l)-fenfluramine is often reduced during MDE. A role for 5-HT in mood modulation has also been proposed, because mood lowering after tryptophan depletion is often observed in subjects with either a family history of depressive episodes or a past history of depressive episodes.

Upregulation of post synaptic $5\text{-}HT_2$ receptors in suicide victims may also suggest that neuronal 5-HT release is low during MDE. The majority of suicide victims have a diagnosis of MDE and some of the post-mortem investigations of $5\text{-}HT_2$ receptors in suicide victims exclusively sampled depressed suicide victims. $5\text{-}HT_2$ receptor density regulates in response to 5-HT changes when MAO-A is inhibited or when tryptophan hydroxylase is inhibited such that decreases in 5-HT are associated with increased $5\text{-}HT_2$ density and increases in 5-HT are associated with decreases in $5\text{-}HT_2$ density.

There is a paucity of imaging studies of $5\text{-}HT_2$ receptors in drug free MDE. Most such studies recruit subjects who were recently withdrawn from medication. Meyer et al. recently published an article in the American Journal of Psychiatry which found increased $5\text{-}HT_2$ BP in MDE with negativistic, pessimistic dysfunctional attitudes.

Although there have been fewer investigations of norepinephrine and dopamine abnormalities during MDE, a number of reports suggest that there could be norepinephrine and dopamine lowering process during MDE as well. Several adrenergic receptor abnormalites found during MDE can occur during norepinephrine lowering processes. These include a significant proportion of investigations reporting increased $\beta_2$ receptor (post-synaptic) density in suicide victims, increased $\alpha_2$ adrenergic receptor density in depressed suicide victims and decreased (presynaptic) norepinephrine transporter density in locus coeruleus. $\alpha_2$ Receptors and $\beta_2$ receptors increase in density under some norepinephrine depleting paradigms. The presynaptic norepinephrine transporter decreases in density when norepinephrine is chronically low. While suicide victims may have a variety of psychiatric diagnoses, the most common is MDE. These findings provide support for a norepinephrine lowering process during MDE.

Indirect investigations of dopamine during MDE suggest that dopamine may be low, especially when motor retardation is present. Increased $D_2$ binding potential (post-synaptic receptor) may occur when extracellular dopamine is low. We currently have an article in press in the American Journal of Psychiatry which found greater $D_2$ BP during MDE with motor retardation [1]. Subjects were medication free for 6 months or more and were non-smoking. There are also some reports of increased $D_2$ BP during MDE in other samples that have not selected medication free subjects. We previously found decreased striatal DAT BP in drug free, non-smoking subjects with MDE [2]. Neumeister et al. found decreased striatal DAT BP in medication subjects with seasonal affective disorder and Klimek et al. report decreased DAT density in amygdala. The DAT, a presynaptic receptor, is reduced after chronic dopamine depletion, thus a reduced striatal DAT BP during MDE is also consistent with a dopamine depleting process during MDE. Decreased cerebrospinal fluid levels of dopamine metabolite homovanillic acid is often reported during MDE with motor retardation. This is also suggestive of low brain dopamine during MDE with motor retardation.

Monoamine oxidase A (MAO-A) is an enzyme found throughout the body. In the brain, a predominant location for this enzyme is on the outer mitochondria membranes in neurons [11]. In the human central nervous system, monoamine oxidase A density is highest in brainstem (locus coeruleus), lower in the hippocampus, cortex, striatum, and minimal in white matter tissue [11].

Serotonin is a high affinity substrate for MAO-A [12, 13]. MAO-A is detectable in serotonin releasing neurons [14]. MAO-A clearly influences extracellular serotonin because administration of MAO-A inhibitors increase extracellular serotonin from 20 to 200 percent, depending upon drug, dose and region [15-17]. This has been found in at least seven separate studies and across five different MAO-A inhibitors (clorgyline, moclobemide, brofaromine, harman, befloxatone) [15-17] and the finding was present in a variety of brain regions including prefrontal cortex, hippocampus, and superior raphe nuclei. In these paradigms it is often demonstrated that brain 5-HIAA is reduced [15]. There is some question as to whether brofaromine is selective, but to our knowledge the other MAO-A inhibitors are considered selective. Extracellular serotonin is also raised substantively (100-200%) in prefrontal cortex, hippocampus and superior raphe nuclei in the knockout model of MAO-A [80].

The effect of MAO-B inhibitors upon extracellular 5-HT, is reported to be more modest than MAO-A inhibitors. After MAO-B inhibition, 5-HT was raised from 0% (non-significant) to 20% [16, 17]. MAO-B inhibitors had the least effect in cortex and greatest (albeit moderate) effect in the raphe nuclei [16, 17].

Norepinephrine is a high affinity substrate for MAO-A. MAO-A is easily detectable in cells that synthesize norepinephrine [11, 14. 19]. Under conditions of MAO-A inhibition, extracellular norepinephrine is increased in prefrontal cortex as well as hippocampus [20, 21] which argues that MAO-A has a substantial role in controlling extracellular norepinephrine in these brain regions. Extracellular norepinephrine is elevated in prefrontal cortex and hippocampus in MAO-A knockout mice [22].

Dopamine is a high affinity substrate for MAO-A [13]. Administration of MAO-A inhibitors increases extracellular dopamine in striatum under baseline conditions as well as during precursor loading paradigms [23, 24]. We are aware of a couple of reports detecting MAO-A in dopamine synthesizing neurons [25], although it has been postulated that MAO-A outside of dopamine synthesizing neurons is more likely to account for the elevations in extracellular striatal dopamine after MAO-A inhibition [11].

The vast majority of longstanding antidepressant medication treatments for major depressive episodes raise monoamines. Most antidepressant medications raise monoamines by inhibiting the reuptake of serotonin, norepinephrine or dopamine. Some antidepressant medications raise monoamines by inhibiting the activity of monoamine oxidase A and/or monoamine oxidase B.

It has been repeatedly demonstrated that medications that raise monoamines such as serotonin reuptake inhibitors, norepinephrine reuptake inhibitors, dopamine reuptake inhibitors and monoamine oxidase inhibitors all can reduce the risk of recurrence of a depressive episode [26]. Since these medications raise monoamines, it follows that there is a relationship between chronic monoamine levels and propensity for recurrence of depressive episodes.

In people with a history of depressive episodes, acute reductions in monoamines are known to temporarily result in recurrence of low mood. The tryptophan depletion paradigm is a comparison of two oral amino acid dosings. One dosing (part A) is the administration of an amino acid mixture that is high in large amino acids yet devoid of tryptophan. The other dosing (part B—control) contains the same amino acid mixture with tryptophan added. They are given in a randomized double blind fashion. By giving a relative deficiency in tryptophan in part A, one obtains a decrease in the transport of tryptophan into the brain. Since tryptophan is the precursor to 5-HT, and since 5-HT itself cannot cross the blood brain barrier, this results in lower brain 5-HT. Changes in mood observed after part A in comparison to part B are attributed to a lower level of 5-HT. The tryptophan depletion paradigm, is associated with recurrence of lower mood, especially in people who have a history of depressive episodes and are in recovery. This has been observed in both medication treated and medication free subjects with a history of major depressive episodes.

Alphamethylparatyrosine (AMPT) is an inhibitor of tyrosine hydroxylase and administration of this medication lowers extracellular norepinephrine (in multiple brain regions) and striatal dopamine. When AMPT given to subjects with a history of depressive episodes, recurrence of sustained low mood is common.

SUMMARY OF THE INVENTION

The present invention relates to the diagnosis and treatment of mood disorders. More specifically, the invention relates to diagnosing, assisting in deciding, or developing treatment for mood disorders, such as major depressive disorders.

It is an object of the invention to provide an improved diagnosis and treatment of mood disorders.

According to the present invention there is provided a method of diagnosing a mood disorder in a live vertebrate comprising, determining whether the level of a monoamine oxidase in the vertebrate is elevated compared to a healthy control subject. The mood disorder may be major depressive disorder.

According to the present invention there is provided a method of monitoring treatment of a mood disorder in a live vertebrate comprising:
 determining a first level of a monoamine oxidase in the vertebrate prior to initiating or during the treatment;
 determining a second level of the monoamine oxidase in the vertebrate, during or after the treatment, at a time subsequent to determination of the first level; and
 comparing the first level with the second level to monitor a change in the level of the monoamine oxidase during the treatment.

According to the present invention there is provided a method for identifying a treatment for a mood disorder in a live vertebrate comprising:
 subjecting a vertebrate suffering from a mood disorder to the treatment;
 determining whether the level of a monoamine oxidase has changed as a result of the treatment;
 selecting the treatment that is effective in reducing or stabilizing a symptom of the mood disorder and that either reduces or does not substantially increase the level of the monoamine oxidase.

According to the present invention there is provided a method for treating depression in a vertebrate in need thereof comprising reducing the level of a monoamine oxidase in the vertebrate.

In an aspect of the present invention the monoamine oxidase may be MAO-A or MAO-B. In another aspect of the invention the mood disorder being assessed or treated may be major depressive disorder. In a further aspect of the present invention the level of the monoamine oxidase can be measured by positron emission tomography of a radiotracer molecule that binds to the monoamine oxidase and the radiotracer molecule may be [11C]Harmine. Alternate radiotracers that may be used include [11C] befloxatone, [11C] clorgyline. A combination of tracers may also be used. The level of monoamine oxidase may also be determined using single photon emission tomography (SPECT) with a radiotracer that binds to MAO, or magnetic resonance imaging in combination with a ligand for MAO coupled with a suitable tracer, for example a tagged MAO-targeting antibody, or monoclonal antibody. In yet another aspect of the invention, the level of the monoamine oxidase may be measured in a specific brain region. In still another aspect of the present invention, the treatment of a mood disorder is selected from the group consisting of medication, cognitive behavioural therapy, interpersonal therapy, exercise, and diet.

In still other aspects of the invention the live vertebrate may be symptomatic for the mood disorder or the vertebrate may be asymptomatic for the mood disorder without previously having been symptomatic the mood disorder. The vertebrate may also be asymptomatic for the mood disorder and may previously have been symptomatic for the mood disorder, with an elevated level of the monoamine oxidase indicating a greater risk for recurrence of symptoms.

The methods of the present invention may be used in the context of any live vertebrate in which monoamine oxidase levels are correlated with a mood disorder, including, without limitation, any mammal, for example, human.

The methods of the present invention may be used in the context of any mood disorder that is correlated with a change in monoamine oxidase levels. A non-limiting example of a mood disorder is depression.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

Figure 1:
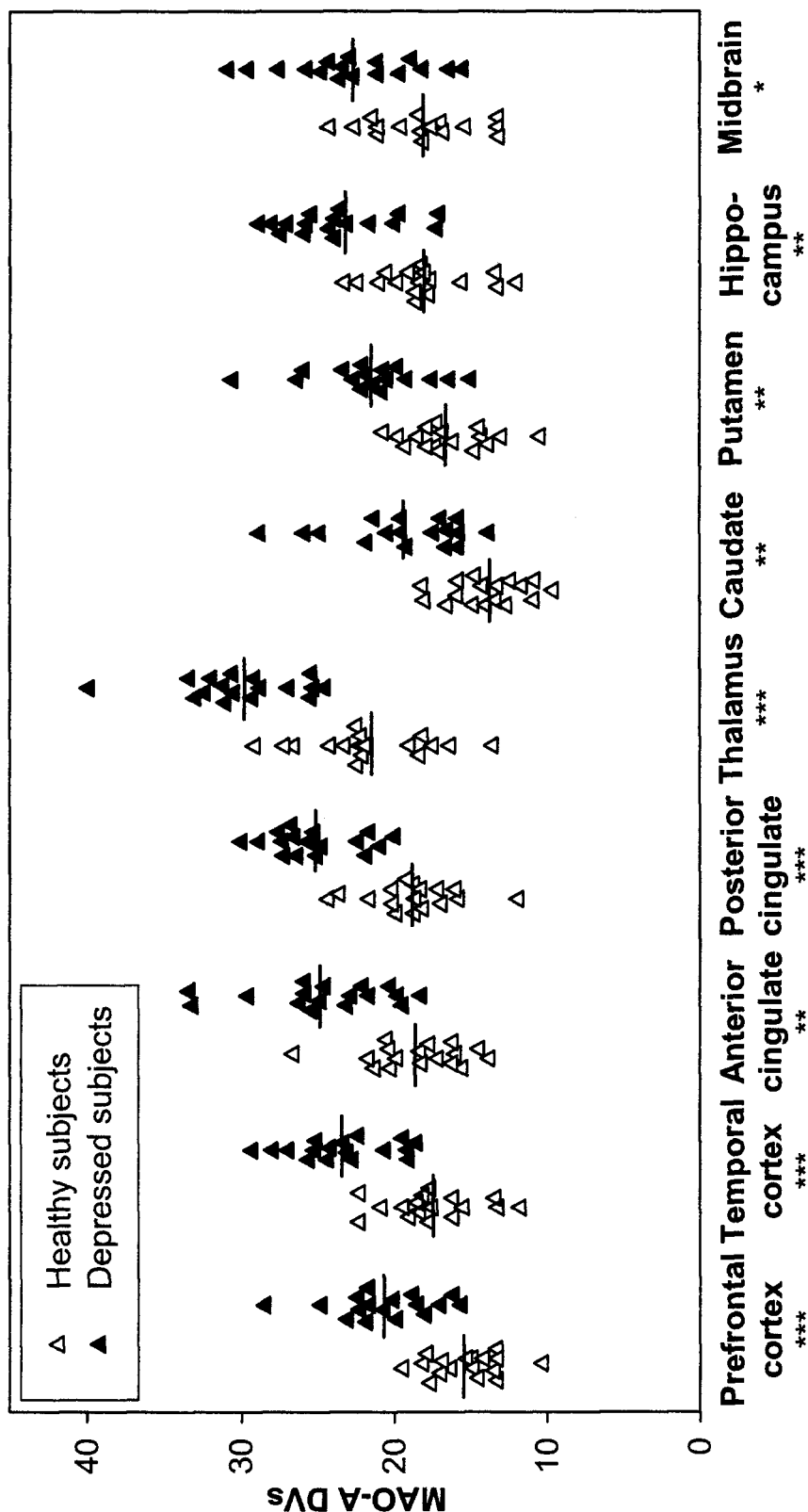
FIG. 1 shows a comparison of MAO-A DVs (Specific Distribution Volume) between depressed and healthy subjects in accordance with an embodiment of the present invention; on average MAO-A DVs was elevated by 34 percent, or two standard deviations, in depressed individuals. Differences between groups were highly significant in each region: * p=0.001,  p<0.0001, * p<0.00001.

The following description is of a preferred embodiment.

The present invention relates to the diagnosis and treatment of psychiatric disorders. More specifically, the invention relates to diagnosing, assisting in deciding, or developing treatment for mood disorders such as major depressive disorders.

The present invention provides a method of diagnosing a mood disorder in a live vertebrate. This method includes determining whether the level of a monoamine oxidase in the live vertebrate is elevated compared to a healthy control subject. The present invention also provides a method of monitoring treatment of a mood disorder in a live vertebrate which involves determining a first level of a monoamine oxidase in the vertebrate prior to initiating or during the treatment; determining a second level of the monoamine oxidase in the vertebrate, during or after the treatment, at a time subsequent to determination of the first level; and comparing the first level with the second level to monitor a change in the level of the monoamine oxidase during the treatment. The present invention also provides a method for identifying a treatment for a mood disorder in a live vertebrate. This latter method involves subjecting a vertebrate suffering from a mood disorder to the treatment; determining whether the level of a monoamine oxidase has changed as a result of the treatment; selecting the treatment that is effective in reducing or stabilizing symptoms of the mood disorder and that either reduces or does not substantially increase the level of the monoamine oxidase. Furthermore, the present invention provides a method for treating depression in a live vertebrate in need thereof comprising, reducing the level of a monoamine oxidase in the vertebrate.

Monoamine oxidase A and Monoamine oxidase B are proteins in the brain that break down monoamines.

There is substantial evidence that monoamines are lowered during MDE (major depressive episodes). In the examples described herein, MAO-A is demonstrated to be highly elevated (34 percent or 2 standard deviations) during MDE. MAO-A metabolizes serotonin, norepinephrine and dopamine in the brain [15-17, 20, 21, 23, 24] so elevated MAO-A can be viewed as an important monoamine lowering process during MDE. Since MAO-A is different during depression, it may be useful in diagnosing depression, or subtypes of depression.

The level (concentration) of monoamine oxidase, such as but not limited to MAO-A or MAO-B, in a live vertebrate may be measured using a radiotracer such as [11C] harmine and positron emission tomography (PET) with arterial sampling [28-31]. Other methods of measuring MAO, for example, MAO-A or other monoamine oxidase, include using radiotracers such as [11C] befloxatone or [11C] clorgyline and (PET) with arterial sampling [32, 33]. An alternative measurement, is to use these radiotracers with PET and venous sampling or no blood sampling at all [29]. By "level" it is meant the amount or concentration (e.g. nano gm/ml; micro gm/ml, or milli gm/ml of sample) of the enzyme or protein. The methods identified above, as well as other methods known in the art, may be used to determine the amount or concentration of a protein in a sample.

Monoamine oxidase, such as but not limited to MAO-A or MAO-B, may alternatively be measured using single photon emission tomography (SPECT) with a radiotracer that binds to MAO-A in combination with arterial blood sampling, venous blood sampling, or no blood sampling at all. This method has been used for measuring other antidepressant target sites, such as the serotonin transporter or the dopamine transporter [34, 35].

Imaging methods PET and SPECT have been compared for neuroimaging in Parkinson's Disease[36]. The key differences between PET and SPECT is that PET has high sensitivity but is not widely available, whereas SPECT has lower sensitivity and is widely available. Although SPECT is of lower sensitivity, it still can be used successfully in diagnostic procedures. In terms of a human brain disorder, SPECT utility has been shown for Parkinson's disease, in which both SPECT and PET imaging (of the dopamine transporter) are helpful in the diagnosis of Parkinson's disease, a condition characterized by loss of dopamine neurons [36].

Another possible method for measuring monoamine oxidase, such as but not limited to MAO-A or MOA-B, is through the use of magnetic resonance imaging coupled with a ligand for the MAO. These methods have been used to measure the amount of bound ligand to serotonin transporters, another target site of antidepressants [38]. Other possible methods for measuring monoamine oxidase levels, such as but not limited to MAO-A or MAO-B, is to measure the MAO itself in blood cells or mRNA for MAO in blood cells. These methods have been used, for example, to measure the serotonin transporter [39-41].

Levels of monoamine oxidase may be measured in a specific brain region, for example one or more of the prefrontal cortex, the termporal corex, the anterior cingulated, the posterior cingulated, the thalamus, the caudate, the putamend, the hippocampus or the midbrain. In the examples described herein MOA concentrations, for example MAO-A DVs, levels were highly significantly elevated in each of the above mentioned brain regions by an average magnitude 34 percent (or two standard devations) in the depressed subjects.

Most antidepressants raise monoamines. Raising monoamines is generally viewed as therapeutic for major depressive episodes so as to make symptoms remit. Raising monoamines is also generally viewed as an approach to prevent symptoms from recurring.

Greater MAO, for example MAO-A, or an increase in the amount of MAO, when compared to the levels of MAO in a healthy subject (control) is a process that is viewed as monoamine lowering. Therefore greater MAO, including greater amounts of MAO-A is a process that may function in opposition to the effects of antidepressants. Thus people who have greater amounts (or concentration) of MAO, MAO-A or MAO-B, when compared to a control subject, may require particular antidepressant dosages and durations of treatment to more optimally reduce symptoms and/or prevent recurrence of illness. Representative treatment examples could involve treatment for symptoms of major depressive episodes or treatment to prevent recurrence of symptoms of major depressive episodes.

Certain representative examples of the present invention relate to:

i) diagnosis of depression;

ii) assistance in choosing antidepressant treatment during periods of symptoms (depressive episodes or depressive episodes not fully remitted);

iii) assistance in choosing antidepressant treatment during periods of being asymptomatic so as to prevent recurrence;

iv) development of novel, monoamine raising treatments.

i) Brain MAO Measurements for Assistance with Diagnosing Depression

We have found elevations in MAO, for example MAO-A, in early onset depression. Therefore, in cases where the diagnosis is unclear, an elevation in MAO, including MAO-A or MAO-B, preferably MAO-A levels could be used to diagnose early onset depression.

ii) Brain MAO Measurements for Assistance in Choosing Antidepressant Treatment During Periods of Symptoms (Either Full Depressive Episodes, or Depressive Episodes not Fully Remitted)

A greater level of MAO, including MAO-A is viewed as monoamine lowering. Therefore greater MAO-A is a process that may function in opposition to the effects of antidepressants. People who have symptoms of depression and very high MAO-A levels may be better treated with a higher dose of a monoamine raising treatment because the high MAO-A would be expected to interfere with the antidepressant treatment.

Antidepressant treatments could include medication, cognitive behavioural therapy, interpersonal therapy, exercise regimens or diet.

iii) Brain MAO Measurements as a Predictor of Depression Recurrence Including Assistance in Choosing Antidepressant Treatment During Asymptomatic Periods to Prevent Recurrence MAO, for example MAO-A, metabolizes monoamines [15-1, 21, 23, 24], and elevated MAO-A may be a monoamine lowering process present in some aysmptomatic depressed individuals. It is suspected that asymptomatic depressed individuals with greater MAO, including MAO-A, will have relatively lower monoamines and be at greater risk for depression.

Asymptomatic depressed individuals with elevated MAO, including MAO-A would be expected to require higher doses for prophylaxis and/or longer periods of prophylaxis to prevent recurrence of symptoms. Antidepressant treatments include medication, cognitive behavioural therapy, interpersonal therapy, exercise regimens or diet.

As shown in the examples disclosed herein, elevations in MAO, including MAO-A or MAO-B and preferably MAO-A, occurs in recovered depressed subjects who have recurrence of MDE symptoms. In some people, there may be a monoamine lowering process that is present in the midst of recovery. Measurement of MAO, including MAO-A, concentrations may therefore be used as a method of predicting recurrence. The advantage of this measurement is that such individuals could obtain particular prophylactic treatments so as to stop recurrence.

Treatments may be used which decrease the levels or amount of MAO, including MAO-A, so as to lower risk of recurrence of depression (especially for people with recurrence of depression despite treatments like cognitive behavioral therapy). In the short term this could involve medications that are available like moclobemide that bind to MAO-A and inactivate it. In the longer term, entirely new treatments could be developed that, after brief dosing periods, reduce the production of excess MAO-A or enhance the removal of MAO-A. Such treatments would be expected to reduce the risk of future depressive episodes.

While MAO-A inhibitor treatments have been shown to work previously, the argument for their use was that they raise monoamines. The results shown in the examples described herein, indicate that MAO, including MAO-A, itself is a pathological marker that relates to risk of recurrence and that targeting of MAO, MAO-A, MAO-B or a combination thereof, is a way to target illness recurrence. Therefore, on this basis, treatments that lower MAO, including MAO-A, by reducing the production of for example, MAO-A or enhancing the removal of MAO-A would be expected to prophylax against recurrence of depressive episodes.

There may also be entirely new ways to reduce the risk of future depressive episodes. For example, it would be useful to avoid environmental causes of elevated MAO, including MAO-A. In general, administration of substrates for enzymes results in induction of more enzyme. It is quite possible that medications that are substrates for MAO-A such as phenylephrine (found in commonly used over the counter nasal decongestants), propanolol, metoprolol, sumatriptan, and flurazepam may induce MAO-A and raise risk of recurrence. It may be that people with a history of depressive episodes should avoid these medications.

iv) Development of Novel Antidepressant

We found in the first subjects studied (n=3) that selective serotonin reuptake inhibitor medications raise MAO-A substantially (approximately 30 percent) in humans. This is likely to be an undesirable effect that reflects a brain counter-response to the antidepressant medication. Not all medications that have serotonin reuptake inhibitor properties may substantially raise MAO-A in humans. Medications that do not raise MAO-A substantially in humans would be expected to have therapeutic advantages.

Increased Monoamine Oxidase a Specific Distribution Volume (MAO-A DVs) in Medication Free Depressed Subjects as Compared to Healthy Subjects MAO-A $DV_S$ is an Index of MAO-A Density: Evidence for Elevated Brain MAO-A Levels in Depression Seventeen depressed and 17 healthy subjects were brain scanned with [$^{11}$C] harmine positron emission tomography (PET). The subjects were otherwise healthy and drug free. Depressed subjects had early onset depression since late onset depression is probably associated with different etiologies of vascular and neurodegenerative disease [3]. Depressed subjects were drug free for at least 3 months although most were antidepressant naive. Depressed subjects were aged 18-50, met DSM-UV diagnosis of current major depressive episode (MDE) and major depressive disorder (MDD) verified by SCID for DSM IV, and a psychiatric consultation, non-smoking [4] and had greater than 17 on the 17 item Hamilton Depression Rating Scale (HDRS).

The MAO-A $DV_S$ is highly significantly elevated (p<0.001 each region, average magnitude 34 percent (or two standard devations)) in the depressed subjects. FIG. 1, attached shows the differences in regional MAO-A DVs between depressed and healthy subjects. The portion of the distribution volume corresponding to the free and non-specific compartment was similar between depressed and healthy subjects. We show this work to argue that MAO-A is elevated in early onset depression.

No Post Mortem Studies of MAO-A in Early Onset, Medication Free, Depression

The inventors are aware of five post-mortem studies of MAO-A in suicide victims, however, this work has not investigated the question as to whether MAO-A is elevated in medication free, early onset depression for the following reasons: a lack of specificity of technique for MAO-A; diagnostic non-specificity by sampling of suicide victims rather than depressed suicide victims; inclusion of subjects who recently took medication, and/or overdosed [5-9]; and no differentiation between early onset depression and late onset depression [5-9]. There is a sixth investigation of monoamine oxidase by Galva et al. [10], however, there were only four subjects with mood disorder in that post mortem study.

Almost all of these post mortem studies did not sample enough people with major depressive disorder depression so their results cannot be considered representative of major depressive disorder. There is one exception: The study by Ordaway et al. [9] was the only study that sampled more than 7 depressed subjects (it sampled 12). This investigation only examined the locus coeruleus. This investigation did not exclusively examine early onset depression and one of the subjects in the sample had Parkinson's disease.

Other studies have shown no difference in MAO-A levels in post mortem brains analyzed 1-3 days after death compared to brains of healthy subjects. Without wishing to be bound by theory, it is believed that post mortem studies show variability in protein levels due to breakdown (i.e. protein turn-over) of proteins after death.

All these studies were carried out on post mortem brains and not on live vertebrate subjects as is the case with the present invention. By providing a method which allows analysis of live vertebrate, the present invention provides a method which can be used to measure real-time MAO levels and diagnose, monitor, and treat mood disorders, such as but not limited to depression.

The present invention will be further illustrated in the following examples.

EXAMPLES

Example 1

Comparison of MAO-A DVs in Multiple Brain Regions Between Recovered MDD Subjects and Healthy Subjects Participants Twenty subjects with a major depressive episode (MDE) and major depressive disorder were recruited and 17 depressed subjects completed the protocol (mean age 34 years, standard deviation (sd) 8 years, 8 male; 9 female). Seventeen age matched healthy subjects were recruited (mean age 34 years, sd 8 years, 10 male; 7 female). Subjects were between 20 and 49 years of age. Healthy subjects were age matched within 4 years to depressed patients (see Table 1).

TABLE 1

Sample Demographics

| Demographic | Healthy Group | Depressed Group |
| --- | --- | --- |
| Total Number | 17 | 17 |
| Mean Age | 34 ± 8 | 34 ± 8 |
| Women | 7 | 9 |
| Men | 10 | 8 |
| Years of Education | 15 ± 2 | 15 ± 2 |
| Psychiatric Diagnosis* | None | Major Depressive Episode, Major Depressive Disorder |
| First Major Depressive Episode | Not Applicable | 8 |
| Second Major Depressive Episode | Not Applicable | 5 |
| Third Major Depressive Episode | Not Applicable | 4 |
| No Previous Antidepressant Trial | Not Applicable | 11 |
| Previous Antidepressant Trial** | Not Applicable | 6 |

*Subjects did not have comorbid axis I disorders nor borderline personality disorder or antisocial personality disorder.
**No subject with depression had received antidepressant treatment within the past 5 months.

All subjects (MDE and healthy) were physically healthy, non-smoking, and had no history of neurotoxin use. Women in perimenopause or in menopause were excluded. Healthy subjects were screened to rule out any axis I disorders and depressed subjects were screened to rule out any comorbid axis I disorders using the structured clinical interview for DSM IV. All subjects were screened to rule out borderline and antisocial personality disorder using the structured clinical interview for DSM IV for axis II disorders [42]. All subjects underwent a urine drug screen on the day of the [11C] harmine PET scan. All depressed subjects underwent common blood tests to rule out medical causes of disturbed mood (thyroid function, electrolytes, complete blood cell count).

For depressed subjects, the mean age of onset of illness was 23 years (sd=10). Subjects were in their first (n=8), second, (n=5) or third (n=4) MDE. No subject with depression had received antidepressant treatment within the past 5 months and 11 depressed patients had never received a trial of antidepressant treatment. For depressed subjects, a diagnosis of MDE secondary to major depressive disorder was based upon the structured clinical interview (SCID) for DSM IV for axis I disorders and a consultation by a psychiatrist. For subjects with MDE, the minimum severity for enrollment was based upon a cutoff score of 17 on the 17 item Hamilton Depression Rating Scale (HDRS). The mean HDRS for subjects with MDE was 22 (sd=3). Additional exclusion criteria included, MDE with psychotic symptoms, bipolar disorder (type I or II), history of self harm or suicidality outside of episodes of depression, and history of alcohol or drug abuse.

For each subject, written consent was obtained after the procedures had been fully explained. The study and recruitment procedures were approved by the research ethics board for human subjects at the Centre for Addiction and Mental Health.

Image Acquisition and Analysis

370 MBq of intravenous [11C]harmine was administered as a bolus for each PET scan. An automatic blood sampling system was used to measure arterial blood radioactivity continuously for the first 10 minutes. Manual samples were taken at 5, 10, 15, 20, 30, 45, 60 and 90 minutes. The radioactivity in whole blood and plasma was measured as described previously [30]. Frames were acquired as follows: 15 frames of 1 minute, then 15 frames of 5 minutes. [11C]harmine was of high radiochemical purity (>96% (mean 98.4%, SD=0.8%; n=34)) and high specific activity (43 TBq/mmol±18 TBq/mmol at the time of injection). PET images were obtained using a GEMS 2048-15B camera (intrinsic in-plane resolution-full width at half maximum=5.5 mm). All images were corrected for attenuation using a $^{68}$Ge transmission scan and reconstructed by filtered back projection using a Hanning filter.

For the brain region of interest each subject had a magnetic resonance imaging (MRI) scan (GE Signa 1.5 T scanner, spin-echo sequence, T1 weighted image; x, y, z voxel dimensions 0.78, 0.78, 3 mm respectively). Regions of interest (ROI) were drawn on magnetic resonance imaging (MRI) scans that were co-registered to each summed [11C]harmine PET image using a mutual information algorithm. The location of the ROI was verified by visual assessment of the ROI upon the summated [11C]harmine PET image. ROI were drawn to sample the prefrontal cortex, anterior cingulate cortex, posterior cingulate cortex, caudate, putamen, thalamus, anterior temporal cortex, midbrain, and a hippocampus and parahippocampal region. The definitions of the regions of interest were similar to our previous investigations [43, 44]. The prefrontal cortex regions (left and right) were drawn in transverse planes extending 32.5 mm in the z axis and included Brodman's areas 9, 10, 46, and part of 8 and 47. The anterior cingulate cortex (Brodman's areas 24 and part of 32) was sampled from adjacent transverse planes extending 26 mm in the z axis. Putamen, and thalamus were drawn within adjacent transverse planes so as to maximally sample the individual structures. These planes extended 13 mm in the z axis. The remaining regions were sampled from adjacent transverse planes which extended 19.5 mm in the z axis. For the temporal cortex, the anterior third of the temporal cortex was sampled and this included Brodman's area 38, and part of 20, 21, 22. The anterior cingulate cortex and the posterior cingulate cortex (part of Brodman's areas 23, 30) were drawn in transverse planes relative to the corpus callosum.

The kinetics of [11C]harmine can be described with an unconstrained two tissue compartment model (described as method B in our previous publication [30]). Highly identifiable fits with the unconstrained two tissue compartment model are obtainable for $DV_S$ [30]. $DV_S$ is an index of specific binding and represents the concentration of specifically bound radiotracer in tissue relative to plasma concentration at equilibrium (In our previous publication $DV_S$ was referred to as DVB [30]). $DV_S$ can be expressed in terms of kinetic rate parameters as:

$$DV_S = \frac{K_1}{k_2} \times \frac{k_3}{k_4}$$

Where $K_1$ and $k_2$ are influx and efflux rates for radiotracer passage across the blood brain barrier and $k_3$ and $k_4$ describe the radioligand transfer between the free and non-specific compartment and the specific binding compartment. ($K_1/k_2$) is similar among different subjects [30].

The [11C] harmine PET measure of MAO-A DVs was previously found to be very reliable: Under test-retest conditions, for the regions evaluated in this study, the mean absolute difference in MAO-A $DV_S$, expressed as a percentage of MAO-A $DV_S$ ranged from 5 to 17 percent (n=6 subjects).

Statistical Analysis

The primary analysis was an independent samples t-test comparing MAO-A $DV_S$ between depressed and healthy subjects for each brain region. Each individual region was examined.

Results

As expected, given previous report of no relationship between age or gender with MAO-A density, there was no relationship between age or gender and regional MAO-A DVs in the samples (analysis of covariance (ANCOVA), effect of age, F1,32=0.3 to 0.001, p=0.5 to 0.98; analysis of variance (ANOVA), effect of gender, F1,32=0.4 to 0.001, p=0.5 to 0.98).

There was a highly significant elevation in MAO-A DVs in all regions in the depressed group as compared to the healthy group (independent sample t-test, p=0.001 to 0.0000003; mean difference in MAO-A DVs between groups was 34 percent; mean effect size 2). This is shown in FIG. 1. As this was not the situation of a single significant finding among a number of non-significant findings, a correction for multiple comparisons was not done.

A multiple analysis of variance (MANOVA) was also done, with regional MAO-A $DV_S$ as the dependent variable, and diagnosis as a predictor variable (Effect of diagnosis: $F_{9,24}$=5.8, p=0.0003).

To examine whether MAO-A $DV_S$ is related to particular clinical characteristics in addition to diagnosis, secondary post-hoc analyses were done using the Pearson correlation coefficient, correlating regional MAO-A $DV_S$ with the following clinical characteristics: duration of illness, episode number, duration of episode, illness severity based upon the 17 item Hamilton Depression Rating Scale Score, and lifetime history of antidepressant treatment. None of the correlations reached the trend level (p<0.1).

The main finding was that MAO-A $DV_S$, the index of MAO-A density, was elevated throughout the brain on average by 34 percent (2 standard deviations). MAO-A metabolizes all three major monoamines (serotonin, norepinephrine, and dopamine) in the brain and no previous study has convincingly explained why monoamines may be low during major depressive episodes, therefore, it is plausible that an elevation in brain MAO-A density is the primary monoamine lowering process during major depressive episodes.

Without wishing to be bound by theory, during a major depressive episode, elevated MAO-A increases the metabolism of monoamines such as serotonin, norepinephrine and dopamine. Thereafter individual monoamine transporter densities have a secondary influence upon specific extracellular monoamine levels. If the monoamine transporter density for a particular monoamine is low, the effect of greater monoamine metabolism upon extracellular monoamine levels is somewhat attenuated resulting in a moderate monoamine loss. Chronic, moderate loss of a particular monoamine in specific brain regions eventually results in a moderate severity of particular symptoms. If the monoamine transporter density for a particular monoamine is not low during a major depressive episode, then the extracellular concentration of the monoamine is severely reduced and symptoms associated with chronic regional loss of that particular monoamine eventually become severe. Elevated MAO-A is a general monoamine lowering process (with no relationship to particular symptoms) whereas the regional density of monoamine transporters has a selective influence upon particular monoamines (with a strong relationship with particular symptoms).

Example 2

Analysis of Association Between Elevated MAO-A in Recovered Depressed Subjects with Recurrence of Depressive Symptoms Scanning Schedule All subjects received one [11C] harmine PET scan.

Subject Criteria

Recovered Depressed Subjects With Major Depressive Disorder: Twelve were recruited. Inclusion criteria were: (i) clear history of at two MDE secondary to major depressive disorder verified by SCID for DSM IV, and a psychiatric consultation (ii) medication free for at least two years (iii) no cognitive behavioural therapy within the previous 3.5 years (iv) 17 item HDRS score of 7 or less (v) age 18-50 (vi) good physical health.

Exclusion criteria were comorbid axis I disorders, comorbid axis II disorders (screened for with Structured Clinical Interview for DSM IV for axis II disorders, use of herbal remedies, cigarette smoking, drug or medication use within six months (+5 half lives of medication), history of substance abuse or any neurotoxin use, history of psychotic symptoms, history of medical illness or test positive on pregnancy test (for women). All subjects received a urine drug screen as well.

Scanning

[11C] Harmine PET: 370 MBq of [11C] harmine was given by intravenous bolus injection in a manner similar to that described by Bergstrom et al. [29]. Arterial sampling was taken continuously for the first 15 minutes at a rate of 5 ml/min for the first 5 minutes and 2.5 ml/min for the next 10 minutes. In addition, 7 ml manual samples was taken at 5 minutes, 10 minutes, 15 minutes, 20 minutes, 30 minutes, 45 minutes, 60 minutes and 90 minutes. Scanning time was one and a half hours. The first 15 frames were acquired over 1 minute. Thereafter, the next 15 frames were acquired over 5 minutes each. Early arterial blood radioactivity levels were counted using an ABSS system. The manual blood samples were counted, then centrifuged and then the whole plasma will be counted. Then the parent and metabolites were measured using HPLC with column capture and switching techniques[45]. This method of PET scanning has been approved by Health Canada and the Research Ethics Board at the Centre for Addiction and Mental Health.

Image Analysis

Time activity Curves: Region of interest data was obtained from the summated [11C] harmine PET images with reference to a co-registered T1 weighted magnetic resonance imaging (MRI) scan. Coregistration was done using the robust measure of mutual information. Region of interest were drawn within prefrontal cortex (sampling Brodmann's area 9, 10, 46), anterior temporal cortex, anterior cingulate, thalamus, and putamen. The definitions of the regions of interest were essentially similar to our previous investigations [43, 44]

Kinetic Modelling

Figure 2:
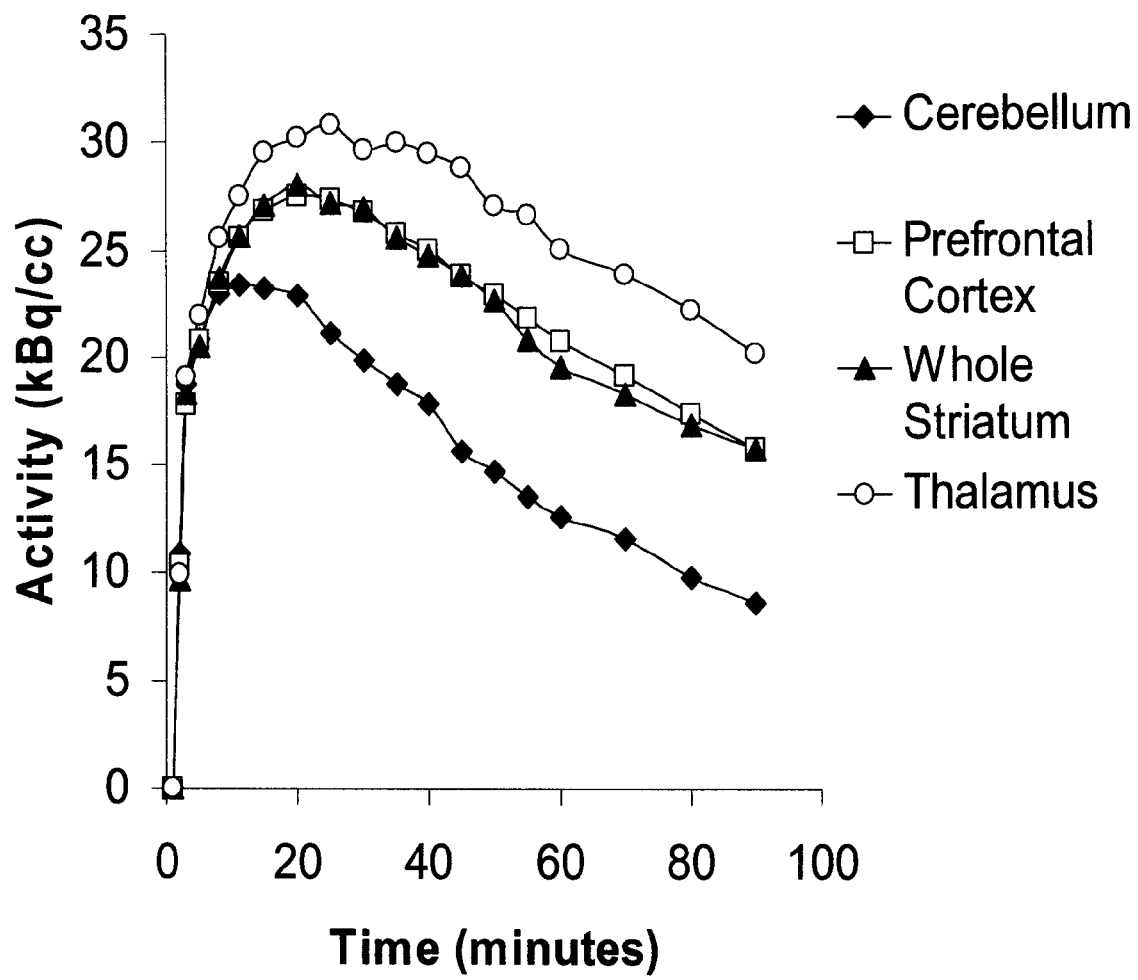
FIG. 2 shows time activity curves for [11C] harmine demonstrating reversible kinetics with typical peaks in radioactivity between 5 and 25 minutes.

[$^{11}$C] harmine is a reversible radiotracer as shown in FIG. 2. We completed the modeling of [$^{11}$C] harmine [30]. There is no reference region (i.e. a region with no specific binding) for [$^{11}$C] harmine so methods involve arterial sampling. The preferred model was the unconstrained two tissue compartment model. With this model, the MAO-A DVs may be measured with excellent identifiability [30].

Kinetic Measurement of MAO-A Specific Distribution Volume (MAO-A $DV_S$): This is a quantitative method of measuring the MAO-A $DV_S$ with [$^{11}$C] harmine PET. A kinetic model was used in which the arterial plasma radioactivity of [$^{11}$C] harmine is an input function and the region of interest data reflects a two tissue compartment model unconstrained [30].

Statistics

In our analyses of the current data set, there is no effect of age upon MAO-A $DV_S$. MAO-A DVs in the recovered depressed was divided into those who had recurrence of symptoms and those who did not. An independent samples t-test was applied to compare regional MAO-A DVs between the two groups.

Results

Figure 3:
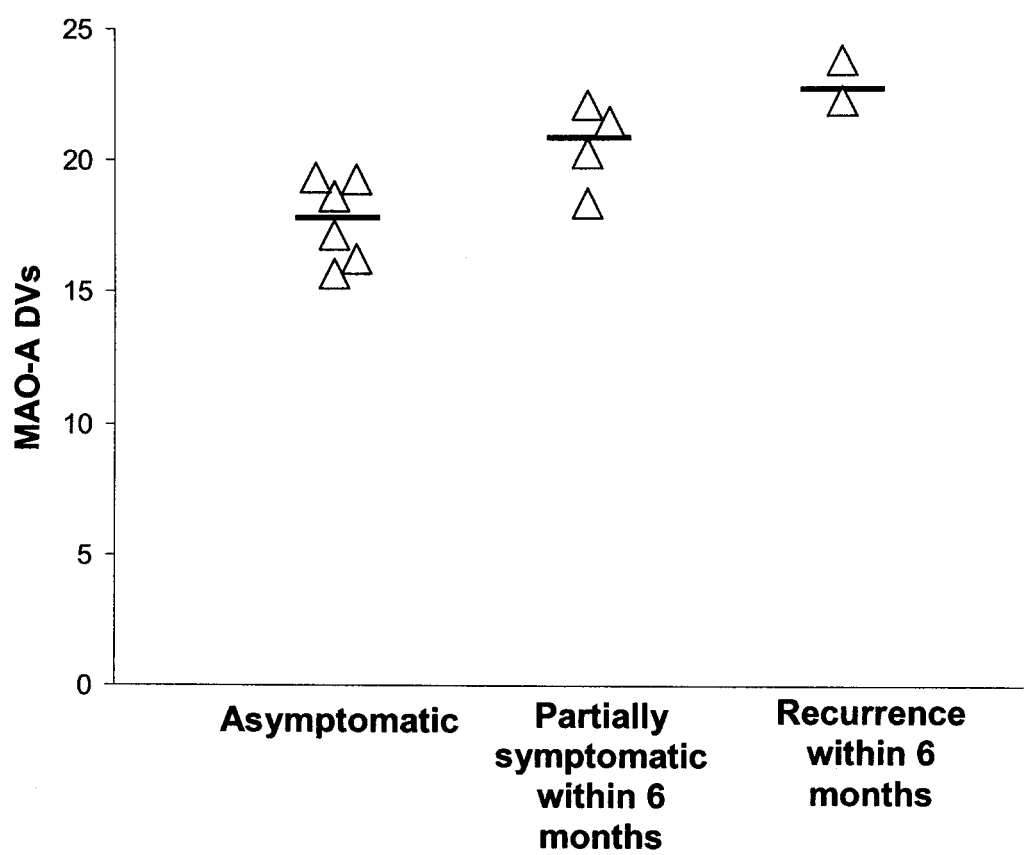
FIG. 3 shows prefrontal MAO-A $DV_S$ in recovered depressed subjects with major depressive disorder. MAO-A $DV_S$ levels in asymptomatic subjects; subjects who are partially symptomatic within 6 months; and subjects with recurrence of disorder within 6 months are shown.

FIG. 3 shows prefrontal MAO-A $DV_S$ levels with respect to recurrence of symptoms. MAO-A $DV_S$ is significantly greater in recovered depressed subjects who subsequently had a recurrence of symptoms within 6 months (t test, n=6 versus n=6, p=0.004). The two subjects with the highest MAO-A $DV_S$ had subsequent full major depressive episodes. Table 2 shows levels of regional MAO-A $DV_S$ in different brain regions with respect to recurrence of symptoms. Across all regions, subjects who had recurrence of symptoms had higher regional MAO-A $DV_S$ values.

TABLE 2

Regional MAO-A $DV_S$ and Risk of Recurrence of Symptoms

| Region | MAO-DVs | | |
| --- | --- | --- | --- |
| | Asymptomatic | Partially symptomatic after 6 months | Recurrence within 6 months |
| Prefrontal Cortex | 17.70 ± 1.56 | 20.49 ± 1.62 | 22.95 ± 1.11 |
| Putamen | 17.61 ± 1.01 | 18.49 ± 3.28 | 23.04 ± 2.87 |
| Thalamus | 26.64 ± 1.95 | 27.17 ± 5.44 | 34.10 ± 1.24 |
| Anterior Cingulate | 19.84 ± 1.70 | 21.40 ± 4.12 | 24.89 ± 0.53 |
| Temporal Cortex | 19.12 ± 2.00 | 20.51 ± 2.81 | 25.06 ± 0.95 |

References

1. Meyer J H, McNeeley H E, Sagrati S, et al. Striatal D2 Receptor Binding Potential and its Relationship to Motor Retardation in Major Depression. Am J Psychiatry in press.
2. Meyer J H, Kruger S, Wilson A A, et al. Lower dopamine transporter binding potential in striatum during depression. Neuroreport 2001; 12(18):4121-5.
3. Krishnan K R. Biological risk factors in late life depression. Biol Psychiatry 2002; 52(3): 185-92.
4. Fowler J S, Volkow N D, Wang G J, et al. Brain monoamine oxidase A inhibition in cigarette smokers. Proc Nati Acad Sci USA 1996; 93(24):14065-9.
5. Grote S S, Moses S G, Robins E, Hudgens R W, Croninger A B. A study of selected catecholamine metabolizing enzymes: a comparison of depressive suicides and alcoholic suicides with controls. J Neurochem 1974; 23(4): 791-802.
6. Gottfries C G, Oreland L, Wiberg A, Winblad B. Lowered monoamine oxidase activity in brains from alcoholic suicides. J Neurochem 1975; 25(5):667-73.
7. Mann J J, Stanley M. Postmortem monoamine oxidase enzyme kinetics in the frontal cortex of suicide victims and controls. Acta Psychiatr Scand 1984; 69(2):135-9.
8. Sherif F, Marcusson J, Oreland L. Brain gamma-aminobutyrate transaminase and monoamine oxidase activities in suicide victims. Eur Arch Psychiatry Clin Neurosci 1991; 241(3):139-44.
9. Ordway G A, Farley J T, Dilley G E, et al. Quantitative distribution of monoamine oxidase A in brainstem monoamine nuclei is normal in major depression. Brain Res 1999; 847(1):71-9.
10. Galva M D, Bondiolotti G P, Olasmaa M, Picotti G B. Effect of aging on lazabemide binding, monoamine oxidase activity and monoamine metabolites in human frontal cortex. J Neural Transm Gen Sect 1995; 101(1-3):83-94.
11. Saura J, Bleuel Z, Ulrich J, et al. Molecular neuroanatomy of human monoamine oxidases A and B revealed by quantitative enzyme radioautography and in situ hybridization histochemistry. Neuroscience 1996; 70(3):755-74.
12. Fowler C, Oreland L. Substrate-Selective Interaction Between Monoamine Oxidase and Oxygen. In: Singer T, Von Korff R, Murphy D, eds. Monoamine Oxidase: Structure, Function, and Altered Functions. New York: Academic Press, Inc., 1979: 145-151.
13. Kinemuchi H, Fowler C, Tipton K. Substrate Specificities of the Two Forms of Monoamine Oxidase. In: Tipton K, Dostert P, Strolin-Benedetti M, eds. Monoamine Oxidase and Disease: Prospects for Therapy with Reversible Inhibitors. New York: Academic Press, Inc., 1984: 53-62.
14. Konradi C, Svoma E, Jellinger K, Riederer P, Denney R, Thibault J. Topographic immunocytochemical mapping of monoamine oxidase-A, monoamine oxidase-B and tyrosine hydroxylase in human post mortem brain stem. Neuroscience 1988; 26(3):791-802.
15. Adell A, Biggs T A, Myers R D. Action of harman (1-methyl-beta-carboline) on the brain: body temperature and in vivo efflux of 5-HT from hippocampus of the rat. Neuropharmacology 1996; 35(8): 1101-7.
16. Celada P, Artigas F. Monoamine oxidase inhibitors increase preferentially extracellular 5-hydroxytryptamine in the midbrain raphe nuclei. A brain microdialysis study in the awake rat. Naunyn Schmiedebergs Arch Pharmacol 1993; 347(6):583-90.
17. Haefely W, Burkard W P, Cesura A M, et al. Biochemistry and pharmacology of moclobemide, a prototype RIMA. Psychopharmacology (Berl) 1992; 106 Suppl:S6-14.
18. Evrard A, Malagie I, Laporte A M, et al. Altered regulation of the 5-HT system in the brain of MAO-A knock-out mice. Eur J Neurosci 2002; 15(5):841-51.
19. Konradi C, Kornhuber J, Froelich L, et al. Demonstration of monoamine oxidase-A and -B in the human brainstem by a histochemical technique. Neuroscience 1989; 33(2): 383-400.
20. Finberg J P, Pacak K, Goldstein D S, Kopin I J. Modification of cerebral cortical noradrenaline release by chronic inhibition of MAO-A. J Neural Transm Suppl 1994; 41:123-5.
21. Finberg J P, Pacak K, Kopin I J, Goldstein D S. Chronic inhibition of monoamine oxidase type A increases noradrenaline release in rat frontal cortex. Naunyn Schmiedebergs Arch Pharmacol 1993; 347(5):500-5.
22. Cases O, Seif I, Grimsby J, et al. Aggressive behavior and altered amounts of brain serotonin and norepinephrine in mice lacking MAOA. Science 1995; 268(5218): 1763-6.
23. Adachi Y U, Watanabe K, Higuchi H, Satoh T, Vizi E S. Oxygen inhalation enhances striatal dopamine metabolism and monoamineoxidase enzyme inhibition prevents it: a microdialysis study. Eur J Pharmacol 2001; 422(1-3):61-8.
24. Wayrnent H K, Schenk J O, Sorg B A. Characterization of extracellular dopamine clearance in the medial prefrontal cortex: role of monoamine uptake and monoamine oxidase inhibition. J Neurosci 2001; 21(1):35-44.
25. Moll G, Moll R, Riederer P, Gsell W, Heinsen H, Denney R M. Immunofluorescence cytochemistry on thin frozen sections of human substantia nigra for staining of monoamine oxidase A and monoamine oxidase B: a pilot study. J Neural Transm Suppl 1990; 32:67-77.
26. Hochstrasser B, Isaksen P M, Koponen H, et al. Prophylactic effect of citalopram in unipolar, recurrent depression: placebo-controlled study of maintenance therapy. Br J Psychiatry 2001; 178:304-10.
27. Fowler J S, MacGregor R R, Wolf A P, et al. Mapping human brain monoamine oxidase A and B with 11C-labeled suicide inactivators and PET. Science 1987; 235 (4787):481-5.
28. Bergstrom M, Westerberg G, Kihlberg T, Langstrom B. Synthesis of some 11C-labelled MAO-A inhibitors and their in vivo uptake kinetics in rhesus monkey brain. Nucl Med Biol 1997; 24(5):381-8.
29. Bergstrom M, Westerberg G, Nemeth G, et al. MAO-A inhibition in brain after dosing with esuprone, moclobemide and placebo in healthy volunteers: in vivo studies with positron emission tomography. Eur J Clin Pharmacol 1997; 52(2):121-8.
30. Ginovart N, Meyer J H, Boovariwala A, et al. Positron emission tomography quantification of [11C]-Harmine binding to monoamine oxidase-A in the human brain. J Cereb Blood Flow Metab 2006; 26:330-344.
31. Bergstrom M, Westerberg G, Langstrom B. 11C-harmine as a tracer for monoamine oxidase A (MAO-A): in vitro and in vivo studies. Nucl Med Biol 1997; 24(4):287-93.
32. Bottlaender M, Dolle F, Guenther I, Roumenov D, Fuseau C, Bramoulle Y, Curet O, Jegham J, Pinquier J L, George P, Valette H. Mapping the cerebral monoamine oxidase type A: positron emission tomography characterization of the reversible selective inhibitor [11C]befloxatone. J Pharmacol Exp Ther 2003; 305:467-473.
33. Fowler J S, MacGregor R R, Wolf A P, Arnett C D, Dewey S L, Schlyer D, Christman D, Logan J, Smith M, Sachs H, et al. Mapping human brain monoamine oxidase A and B with 11C-labeled suicide inactivators and PET. Science 1987; 235:481-485.
34. Erlandsson K, Sivananthan T, Lui D, Spezzi A, Townsend C E, Mu S, Lucas R, Warrington S, Ell P J. (2005) Measuring SSRI occupancy of SERT using the novel tracer [123I]ADAM: a SPECT validation study. Eur J Nucl Med Mol Imaging 32:1329-1336.
35. Prunier C, Payoux P, Guilloteau D, Chalon S, Giraudeau B, Majorel C, Tafani M, Bezard E, Esquerre J P, Baulieu J L. (2003) Quantification of dopamine transporter by 123I-PE2I SPECT and the noninvasive Logan graphical method in Parkinson's disease. J Nucl Med 44:663-670.
36. Brooks D (2004) Neruoimaging in Parkinson's Disease. J American Society for Experimental NeuroTherapeutics 1: 243-254.
37. Bolo N R, Hode Y, Nedelec J F, Laine E, Wagner G, Macher J P. (2000) Brain pharmacokinetics and tissue distribution in vivo of fluvoxamine and fluoxetine by fluorine magnetic resonance spectroscopy. Neuropsychopharmacology 23:428-438.
38. Henry M E, Moore C M, Kaufman M J, Michelson D, Schmidt M E, Stoddard E, Vuckevic A J, Berreira P J, Cohen B M, Renshaw P F. (2000) Brain kinetics of paroxetine and fluoxetine on the third day of placebo substitution: a fluorine MRS study. Am J Psychiatry 157:1506-1508
39. Hranilovic D, Lesch K P, Ugarkovic D, Cicin-Sain L, Jernej B. (1996) Identification of serotonin transporter mRNA in rat platelets. J Neural Transm 103:957-965.
40. Iga J, Ueno S, Yamauchi K, Motoki I, Tayoshi S, Ohta K, Song H, Morita K, Rokutan K, Ohmori T. (2005) Serotonin transporter mRNA expression in peripheral leukocytes of patients with major depression before and after treatment with paroxetine. Neurosci Lett 389:12-16.
41. Malison R T, Price L H, Berman R, van Dyck C H, Pelton G H, Carpenter L, Sanacora G, Owens M J, Nemeroff C B, Rajeevan N, Baldwin R M, Seibyl J P, Innis R B, Chamey D S. (1998) Reduced brain serotonin transporter availability in major depression as measured by [123I]-2 beta-carbomethoxy-3 beta-(4-iodophenyl)tropane and single photon emission computed tomography [see comments]. Biol Psychiatry 44:1090-1098.
42. Blais M A, Norman D K. A psychometric evaluation of the DSM-IV personality disorder criteria. J Personal Disord. 1997; 11(2):168-176.

43. Meyer J H, Houle S, Sagrati S, et al. Brain serotonin transporter binding potential measured with carbon 11-labeled DASB positron emission tomography: effects of major depressive episodes and severity of dysfunctional attitudes. Arch Gen Psychiatry. December 2004; 61(12): 1271-1279.
44. Meyer J H, McMain S, Kennedy S H, et al. Dysfunctional Attitudes and 5-HT(2) Receptors During Depression and Self-Harm. Am J. Psychiatry. 2003; 160(1):90-99.
45. Wilson A, Meyer J, Garcia A, Singh K, Hussey D, Houle S, Ginovart N: Determination of the Arterial Input Function of the MAO-A Inhibitor [11C] Harmine in Human Subjects. Neuroreceptor Mapping (abstract) 2003.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A method of diagnosing a mood disorder in a live vertebrate comprising:
    a) administering to the live vertebrate a traceable compound that binds monoamine oxidase A (MAO-A) in the brain of the live vertebrate;
    b) quantitatively measuring MAO-A concentration in the brain of the live vertebrate by quantitatively measuring the traceable compound bound to the monoamine oxidase, and;
    c) correlating the measured MAO-A concentration in the brain of the live vertebrate to a control group which does not have mood disorder in order to diagnose mood disorder in the live vertebrate.

2. The method of claim 1, wherein the concentration of the monoamine oxidase is measured by positron emission tomography of a radiotracer molecule that binds to the monoamine oxidase.

3. The method of claim 2, wherein the radiotracer molecule is [$^{11}$C]Harmine.

4. The method of claim 1, wherein the concentration of monoamine oxidase is measured in one or more brain regions.

5. The method of claim 1, wherein the vertebrate is symptomatic for the mood disorder.

6. The method of claim 1, wherein the vertebrate is asymptomatic for the mood disorder and has not previously been symptomatic for the mood disorder.

7. The method of claim 1, wherein the vertebrate is asymptomatic for the mood disorder and has previously been symptomatic for the mood disorder, with an elevated level of monoamine oxidase indicating a greater risk for recurrence of symptoms.

8. A method of monitoring treatment of a mood disorder in a live vertebrate comprising:
    a) administering to the live vertebrate a first traceable compound that binds monoamine oxidase A (MAO-A) in the brain of the live vertebrate;
    b) quantitatively measuring a first concentration of MAO-A in the brain of the vertebrate, by quantitatively measuring the first traceable compound bound to the first concentration of MAO-A, prior to initiating or during the treatment;
    c) administering to the live vertebrate a second traceable compound that binds a second concentration of MAO-A in the brain of the live vertebrate;
    d) quantitatively measuring a second concentration of MAO-A in the brain of the live vertebrate, by quantitatively measuring the second traceable compound bound to the second concentration of MAO-A, during, or after the treatment, at a time subsequent to administering the first traceable compound, and;
    e) comparing the first concentration of MAO-A with the second concentration of MAO-A to monitor a change in the concentration of MAO-A during the treatment.

9. The method of claim 8, wherein the vertebrate is symptomatic for the mood disorder.

10. The method of claim 8, wherein the vertebrate is asymptomatic for the mood disorder and has previously been symptomatic for the mood disorder, with an elevated concentration of the monoamine oxidase indicating a greater risk for recurrence of symptoms.

11. A method for identifying a treatment for a mood disorder in a live vertebrate comprising:
    a) administering to the live vertebrate a first traceable compound that binds monoamine oxidase A (MAO-A) in the brain of the live vertebrate;
    b) quantitatively measuring a first concentration of MAO-A in the brain of the vertebrate, by quantitatively measuring the first traceable compound bound to MAO-A, prior to initiating or during the treatment;
    c) subjecting the live vertebrate suffering from the mood disorder to the treatment;
    d) administering to the live vertebrate a second traceable compound that binds MAO-A in the brain of the live vertebrate;
    e) quantitatively measuring a second concentration of MAO-A in brain of the live vertebrate, by quantitatively measuring the second traceable compound bound to MAO-A, during or after the treatment, at a time subsequent to administering the first traceable compound;
    f) comparing the first concentration of MAO-A with the second concentration of MAO-A to monitor a change in the concentration of MAO-A during the treatment, wherein a lower second concentration of MAO-A relative to the first concentration of MAO-A measured is indicative of a treatment that reduces MAO-A concentration, and;
    g) selecting the treatment that effectively reduces or stabilizes symptoms of the mood disorder and that either reduces or does not increase the concentration of the monoamine oxidase.

12. The method of claim 11, wherein the treatment is selected from the group consisting of medication, cognitive behavioral therapy, interpersonal therapy, exercise, and diet.

13. A method of diagnosing a mood disorder in a live vertebrate comprising:
    a) administering to the live vertebrate a radiotracer compound that binds MAO-A in the brain of the live vertebrate
    b) quantitatively measuring MAO-A concentration in a brain region of the live vertebrate by quantitatively measuring the radiotracer compound bound to MAO-A by positron emission tomography (PET), or single photon emission tomography (SPECT) with arterial sampling, venous sampling or no sampling, and;
    c) correlating the measured MAO-A concentration in the brain of the live vertebrate to a control group which does not have mood disorder in order to diagnose mood disorder in the live vertebrate.

14. The method of claim 1, wherein MAO-A concentration is quantitatively measured by calculating the monoamine oxidase A specific distribution volumes (MAO-A DVs) in a plurality of regions in the brain of the live vertebrate by positron emission tomography (PET).

\* \* \* \* \*